United States Patent [19]

Austad

[11] Patent Number: 5,005,591
[45] Date of Patent: Apr. 9, 1991

[54] SELF-INFLATING TISSUE EXPANDER

[76] Inventor: Eric D. Austad, 309 Riverview Dr., Ann Arbor, Mich. 48104

[21] Appl. No.: 518,489

[22] Filed: May 3, 1990

[51] Int. Cl.$^5$ .......................... A61B 19/00; A61F 2/12; A61F 2/02
[52] U.S. Cl. .......................... 128/899; 623/8; 623/11
[58] Field of Search .................. 623/7, 8, 11; 128/899, 128/898

[56] References Cited

U.S. PATENT DOCUMENTS

| 4,157,085 | 6/1979 | Austad | 623/898 |
|---|---|---|---|
| 4,217,889 | 8/1980 | Radovan et al. | 623/8 X |
| 4,574,780 | 3/1986 | Manders | 128/899 X |
| 4,685,447 | 8/1987 | Iversen et al. | 128/899 |
| 4,899,764 | 2/1990 | Gauger et al. | 128/899 |

Primary Examiner—Ronald Frinks
Attorney, Agent, or Firm—Harness, Dickey & Pierce

[57] ABSTRACT

A surgically implanted device for expanding soft tissues for subsequent use in surgery. The device consists of an envelope portion constructed of a material that is substantially impermeable to extracellular body fluids. A window portion is attached to the envelope and constructed of a material which is readily permeable by extracellular body fluids. An osmotic agent is disposed within the device and induces an osmotic differential across the window portion causing extracellular body fluids to be drawn into the device. As increasing amounts of extracellular fluid are drawn into the device, the material of the envelope expands and subsequently causes the overlying tissue to also expand. A substantially rigid base may be provided to limit the direction of this expansion. The window and osmotic agent may also be incorporated into a remotely positioned fill port. The fill port is connected to the envelope by a conduit which permits the transfer of fluid from the port to expand the envelope.

20 Claims, 3 Drawing Sheets

SELF-INFLATING TISSUE EXPANDER

BACKGROUND AND SUMMARY OF THE INVENTION

The invention relates generally to surgically implanted devices, and particularly to a surgically implanted self-inflating tissue expander. The invention is capable of expanding skin tissues, mucous membranes, and various other soft tissues, thus allowing subsequent use of these tissues for reconstructive surgery.

It is well known that soft tissue, such as skin, muscle, and mucous membrane, has the ability to expand in order to accommodate the growth of underlying structures. One readily known example is the expansion of abdominal skin and muscle during pregnancy or progressive obesity.

Prior art in the medical world has taken advantage of this observed phenomenon. One such device is the tissue expander of U.S. Pat. No. 4,157,085 issued June 5, 1979 to Austad, the applicant in the present application.

In the above mentioned patent, a sealed envelope, constructed of a material permeable to extracellular body fluids, is surgically implanted adjacent to a site in need of tissue for reconstructive surgery or the like. Silicone rubber is used as an envelope material because of its relative strength and flexibility at the useful thicknesses and its biological compatibility with the human body. A material which establishes a high osmotic pressure is placed within the envelope. This induces the passage of extracellular body fluid into the envelope. Salts, such as sodium chloride, are most useful as the osmotic agent because of the high osmotic pressure they develop and their failure to degrade the envelope material. A quantity of salt is placed within the envelope so as to result in a constant saturated solution. The amount of salt needed will vary depending upon the desired inflation rate and the required final expanded volume.

While the above mentioned invention has shown experimental success, several faults have also been discovered. One is in the use of silicone as the envelope material. In thicknesses adequate for product safety, silicone is relatively impermeable to extracellular water. In order to compensate for the required silicone thickness and allow for timely inflation of the tissue, the implant must contain an inordinately high amount of solute.

A second limitation of the above mentioned patent follows from the first. Rupture of the implanted envelope could result in the dispersion of the highly concentrated solute into the surrounding tissues. If the rupture occurred at or shortly after implantation of the envelope, no adverse effect would occur. However, a rupture occurring after the envelope has approached full inflation would result in severe damage to the overlying tissue. This is believed to occur because of a "jet-stream" dispersion of the saturated salt solution into the overlying tissues, rapidly bathing them with the concentrated solution.

It is an object of the present invention to provide a self-inflating tissue expander which is highly permeable to extracellular water and also provides the required characteristics of elasticity, durability and compatibility. Additionally, the tissue expander must also be relatively impermeable to the solute contained therein. By providing a tissue expander that is highly permeable to extracellular water, the solute concentration level can be reduced to a level that is bio-compatable with the surrounding tissues, even in the unlikely event of a rupture at full inflation.

The present invention incorporates a window portion into the design of a tissue expander. The window portion is highly permeable to extracellular water, while the remaining portion of the implant is generally impermeable to this water. Thus, a significant percentage of the inflation (80-90%) occurs through the window. Both portions, however, must be relatively impermeable to the solute contained within the tissue expander. So constructed, the window-type tissue expander offers great latitude in the choice of implant inflation rates through the manipulation of several variables, including the following: the type of material used for the window, the thickness of the material used for the window, the surface area of the window, and the amount of solute placed within the implant. The window may be incorporated directly into the envelope of the implant, or alternatively, it may be remotely joined to the envelope by a connecter tube.

Two variations on the incorporated-window, self-inflating tissue expander include an implant comprised of two or more separate membrane species and an implant consisting of a single membrane species. The first variation incorporates several types of membranes, each having different characteristics. One or more membranes of a highly permeable material form the window portion of the implant. Inflation of the tissue expander occurs primarily through this region. The second variation of the incorporated-window tissue expander is one composed entirely of a single membrane. The membrane in the window portion of the implant is physically modified to enhance its permeability characteristics without significant loss of other desired characteristics. This window may be a single discrete region of the implant or a number of smaller regions intermittently positioned on the implant.

To facilitate manufacturing and give a Doctor greater control and flexibility with regard to inflation rates, the window portion of the self-inflating tissue expander may be constructed as an interchangeable, remote filling port. The remote window being in communication with the interior of the expandable envelope via a connecting tube.

Additional benefits and advantages of the present invention will become apparent to those skilled in the art to which the invention relates from the subsequent description of the preferred embodiments and the appended claims, taken in conjunction with the accompanying drawings.

DETAILED DESCRIPTION OF THE DRAWINGS

Figure 1:
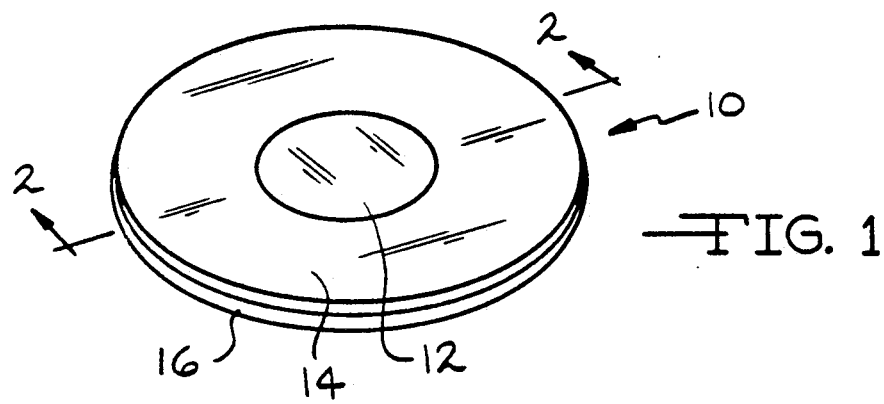
FIG. 1 is a perspective view of the incorporated-window, self-inflating tissue expander of the present invention.
Figure 2:
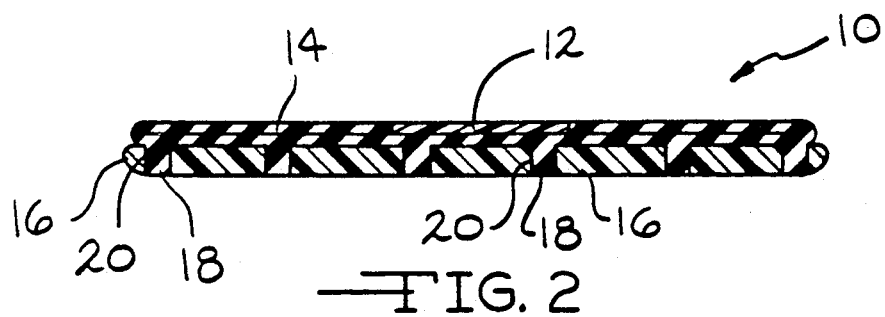
FIG. 2 is a cross-sectional view taken generally along lines 2—2 in FIG. 1 of the tissue expander of the present invention.

Now referring to the drawings, one embodiment of the self-inflating tissue expander 10 of the present invention is comprised of a window portion 12, an envelope portion 14 and, if desired, a base 16. While FIG. 1 shows the tissue expander 10 in a circular configuration, the overall shape of the tissue expander 10 may be modified so as to promote the local expansion of tissues as dictated by the surgery to be performed.

The window 12 is secured to the envelope 14, over an opening in the envelope 14, by a medical adhesive or other conventional method known within the field. Taken together, the window 12 and the envelope 14 form an expandable balloon structure 26 for containing an osmotic agent. While the window 12 is highly permeable to extracellular water, both the window 12 and the envelope 14 must be relatively impermeable to the solute 25 therein containing the osmotic agent 24.

The window 12 is constructed of the synthetic thermoplastic polymer, polysulfone. However, other highly permeable materials might also be employed. Polysulfone is commercially available in various forms. A form of polysulfone highly suitable for the window 12 of the tissue expander 10 is one having a permeability cut-off (upper limit) at a molecular weight of 10,000. In this manner, the majority of the extracellular water (80–90%) entering the tissue expander 10 passes through the window 12. By manipulating the thickness and the overall surface area of the window 12, a desired tissue expander inflation rate can be maintained.

The envelope 14 of the tissue expander 10 is constructed of silicone rubber. Silicone, while relatively impermeable to extracellular water, provides the physical characteristics of elasticity and durability required of the tissue expander during implantation and operation. Other materials, having characteristics similar to those of silicone, might also be employed.

An osmotic agent 24 is contained within the balloon 26 formed by the window 12 and the envelope 14. The osmotic agent 24 may be any solid or liquid which will develop an adequate osmotic differential across the window 12 of the tissue expander 10. The osmotic agent 24 must also be such that it will not degrade the physical characteristics of the material of either the window 12 or the envelope 14.

Numerous substances exist which are useful as osmotic agents 24. These include salts, non-ionic substances, hydrophillic polymers, proteins, and numerous mixtures of these substances. Albumin, a water soluble protein having a molecular weight of 60 000, is a preferred osmotic agent 24 for use with a polysulfone window 12. Because of the high osmotic pressure it provides, sodium chloride is another preferred osmotic agent. The amount of the particular osmotic agent 24 needed will vary depending upon the desired inflation rate, the surface area of the window 12, the permeability of the material used in the window 12, and the desired final expanded volume of the tissue expander 10.

In that expanded tissue may be used for superficial reconstructive surgery, it might be desirable to limit the expansion of the implant to a direction generally outward from the body. To accomplish this goal, the tissue expander 10 can be provided with a resilient base 16. As with the window 12 and envelope 14, the base 16 must also be of a bio-compatible material. Again, silicone is preferred, but polyurethane and other materials can be employed. The resiliency or rigidity of the base 16 can be altered as necessary by varying the thickness of the material employed.

When employed, the base 16 is fixably attached to the envelope 14 so as to allow the window 12 to be in contact with the subcutaneous space. The envelope 14 may be secured to the base 16 by various means, including frictional engagement or the use of a medical adhesive applied to the contacting surfaces of the envelope 14 and the base 16. In one embodiment of the present invention, numerous projections 18 are provided on that portion of the envelope 14 in contact with the base 16. The projections 18 are frictionally or adhesively retained within receiving cavities 20 correspondingly positioned throughout the base 16. It should be noted that in an additional embodiment, the window 12 could be positioned in the base 16 itself.

Figure 6:
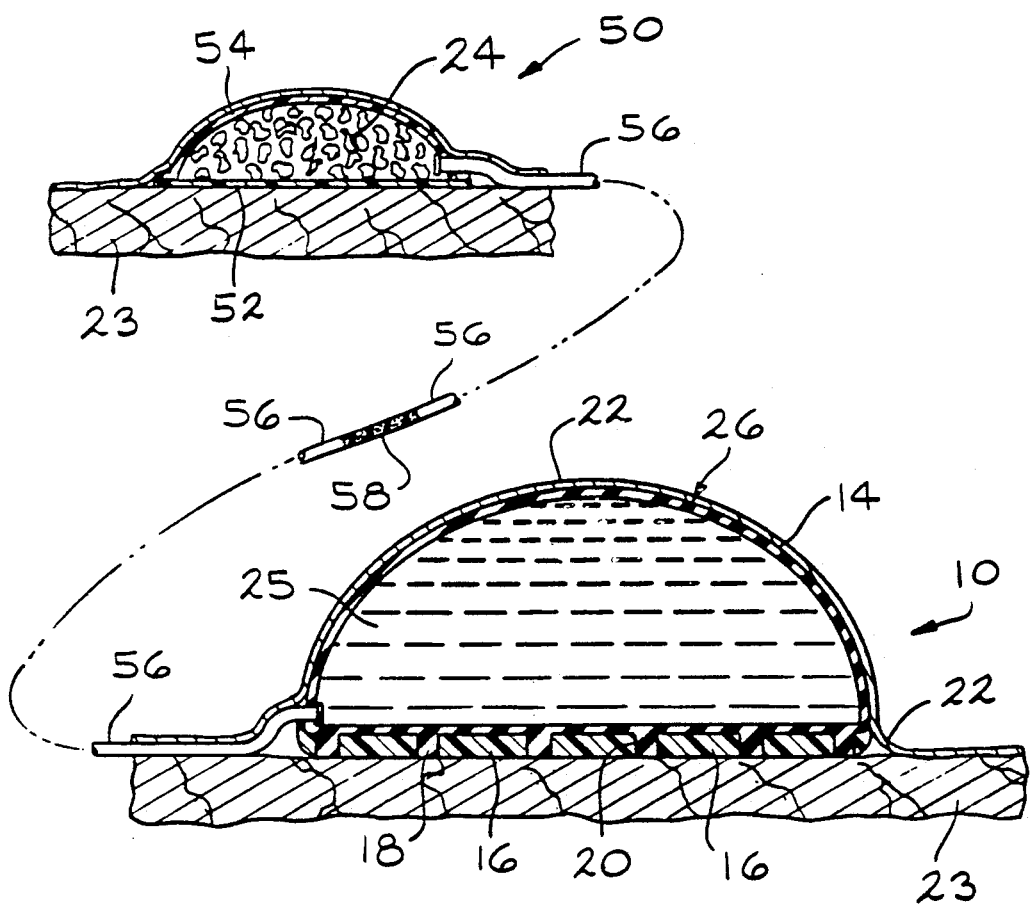
FIG. 6 is a perspective view of the remote-window, self-inflating tissue expander of the present invention.

FIG. 6 illustrates a remote port 50 embodiment of the present invention. The remote port self-inflating tissue expander 50 contains many of the features previously discussed and, where appropriate, incorporates like references. In the remote port 50 embodiment, a remotely connected window 52 incorporated into an otherwise impermeable filling port body 54. The interior of the port body 54 contains the osmotic agent 24 and is in communication with the interior of the expandable balloon 26, now comprised solely of the envelope 14, via a connector tube 56. The length of the connector tube may be varied by removing an appropriate segment and joining the cut ends with readily available connecters. Moreover, remote filling ports 50 exhibiting differing inflation characteristics may be interchanged prior to and after implantation by means of these connectors thereby giving the surgeon greater discretion in the selection of an appropriate inflation rate for the specific clinical situation.

In a scavaging embodiment, the connecter tube 56 may contain an in-line filter 58 which is permeable to extracellular water and only moderately permeable to the osmotic agent 24. This causes the envelope 14 to inflate with a solute 25 of reduced osmotic content, as compared to the solution contained within the interior of fill port 50. To achieve filling of envelope 14, the hydrodynamic requirements of the system are readily met: the in-line filter 58 must be more permeable to the solute 25 containing the osmotic agent 24 than the remote window 52. This scavaging effect is desirable for two reasons. First, it reduces the amount of osmotic agent 24 required to be contained by fill port 50. Second, it reduces the osmotic content of the solute 25 which will subsequently inflate the envelope 14 connected to the remote port 50. As the second reason indicates, the possible damage caused to the tissue by a rupture of the envelope 14 is thereby significantly reduced.

Figure 3:
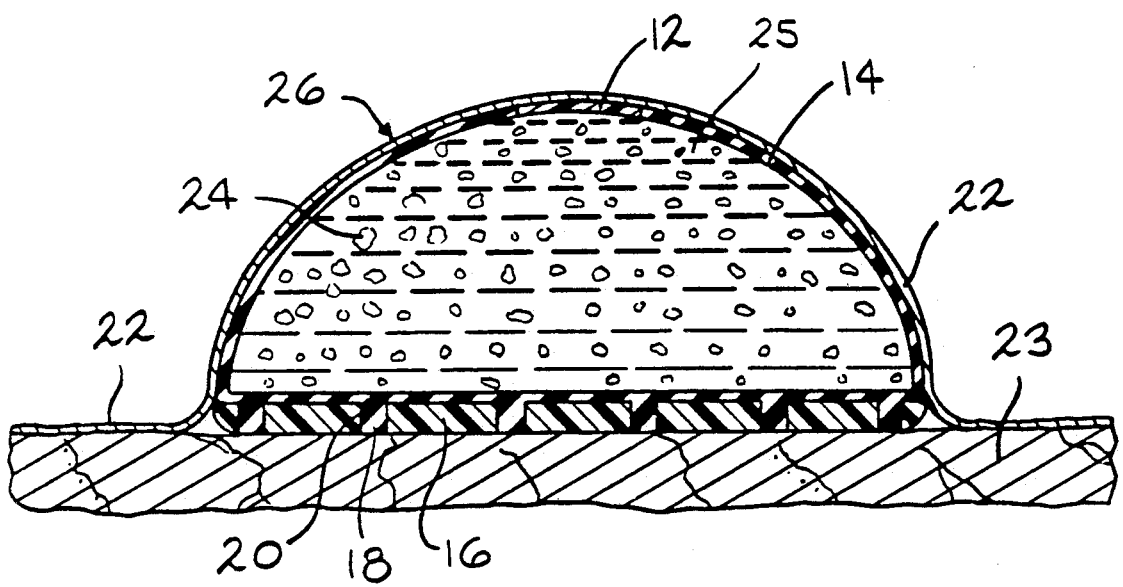
FIG. 3 is a cross-sectional view of a fully expanded tissue expander after surgical implantation in tissue.

In all of the embodiments, once the tissue expander 10 has been implanted in the tissue 22 sought to be expanded, extracellular water will be drawn through the window 12 or 52 and cause the balloon 26 formed by the envelope 14 to swell. As a consequence, the overlying tissue 22 is also expanded. As best seen in FIGS. 3 and 6, if employed, the base 16 will prevent any expansion into the subcutaneous tissues 23. The solute 25 contained within the balloon 26 may vary between being super saturated, saturated and non-saturated, depending upon the amount of osmotic agent 24 and extracellular water contained within the balloon 26 at the given time.

Another embodiment of the tissue expander 10 is one in which the window 12 and the envelope 14 are constructed of the same material. In this embodiment, the material becoming the window portion 12 is regionally or diffusely treated so as to physically modify and enhance its permeability characteristics. For example, in working thicknesses, 0.010 to 0.020 inches (0.254 mm to 0.508 mm), silicone is relatively impermeable to water. However, various methods of modification can be used to alter this permeability.

One method of modification that can be used to increase the permeability of the window portion 12 of the tissue expander 10 is to reduce the thickness of the material located therein. For example, by reducing the working thickness of the silicone in the window 12 from 0.020 inches (0.508 mm) to a thickness between 0.002 inches (0.051 mm) and 0.008 inches (0.203 mm), the permeability of silicone is enhanced by a factor of 4–10.

Another method of modification for increasing the permeability of the window portion 12 is accomplished during fabrication of the implant 10. In this method salts, such as sodium chloride or polyvinyl pyrolidone, are added during fabrication so as to be suspended in the material forming the window 12 or diffusely suspended throughout the entire envelope 14 itself.

Figure 4:
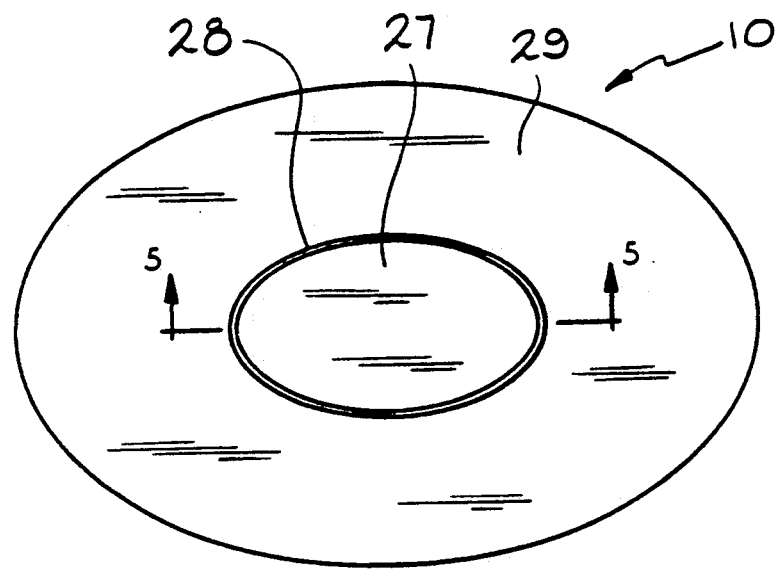
FIG. 4 is a plan view of another embodiment of the tissue expander of the present invention.
Figure 5:
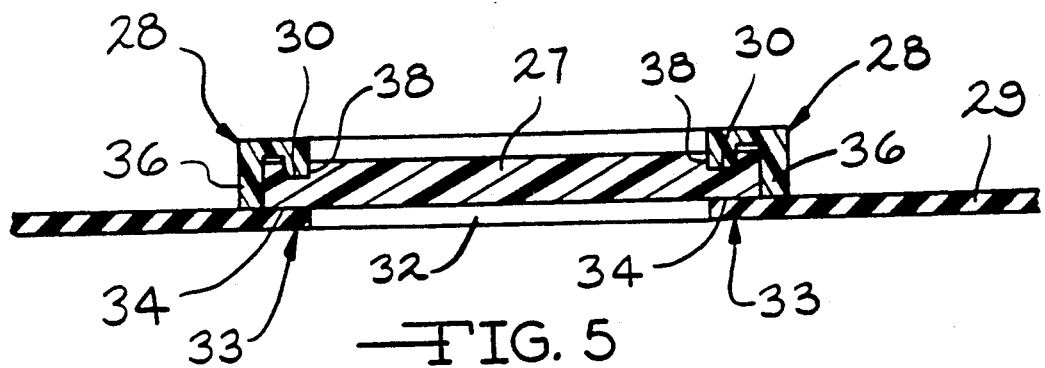
FIG. 5 is a cross-sectional view generally taken along lines 5—5 in FIG. 4 of the window portion of one embodiment of the present invention.

A further embodiment of the present invention, depicted in FIG. 4, consists of a window 27 attached to an envelope portion 29 by a semi-rigid or rigid frame 28. The window 27 and envelope 29 are of the materials and construction previously discussed. The frame 28 is constructed of a material providing substantial rigidity, such as thick silicone or polyurethane, and could be integrally formed with the envelope 29 or attached thereto by various means, including adhesives.

The frame 28 extends upwardly from the outer surface of envelope portion 29, along the perimeter of the window portion 27, shaped in a general hook configuration. The exterior dimensions of the window 27 are greater than the dimensions of a corresponding window opening 32 in the envelope 29 and enable an overlap 34 to occur between the perimeter of the window 27 and the perimeter region 33 of the window opening 32. Thus positioned, a shank 36 of the frame 28 circumscribes the window 27 allowing the frame 28 to generally hook over the perimeter of the window 27. A terminal end 30 of the frame 28 extends back toward the perimeter region 33 of window opening 32 in the envelope 29 and engages a notch 38 correspondingly positioned in the perimeter of the window 27. The terminal end 30 of the frame 28, the overlap 34 of the window 27 and the envelope 29, and the notch 38 coact so as to securely retain the window 27 over the window opening 32. The window 27 may be further secured by the use of medical adhesive in the area of the overlap 34 and the notch 38. Conversely, when a base 16 is employed, the window 27 may be located in the base 16 of the implant 10 and affixed in a similar fashion.

Such an incorporation of the frame 28 into the tissue expander 10 prevents lateral elongation and distortion of the window 27 during the subsequent expansion of the envelope 29. If necessary, a reinforcement structure (not shown), one which would not inhibit the permeability of the window 27 such as nylon netting, could be incorporated exteriorly of the window portion 27 and also be retained by the frame 28. Such a reinforcement structure would further prevent deformation of the window 27 as the tissue expander 10 reaches full inflation.

While the above description constitutes the preferred embodiments of the present invention, it will be appreciated that the invention is susceptible to modification, variation and change without departing from the proper scope and fair meaning of the accompanying claims.

I claim:

1. A surgically implantable self-inflating device for expanding soft tissue without substantial physician manipulation after implantation, said device comprising:
   an expandable envelope portion being substantially impermeable to extracellular body fluids;
   a window portion being readily permeable to extracellular body fluids; and
   an osmotic material disposed within said device and providing an osmotic potential across said window for drawing extracellular fluid therethrough and into said envelope thereby forming a solution with said osmotic material and causing said device to inflate and the overlying tissue to expand.

2. A surgically implantable device for expanding soft tissues as set forth in claim 1 wherein said device further comprises a remotely positioned fill port having said window portion formed therein and containing said osmotic material, conduit means for connecting said fill port to said envelope portion whereby said solution is transferred from said fill port to said envelope portion thereby expanding said envelope portion and overlying tissue.

3. A surgically implantable device for expanding soft tissues as set forth in claim 2 wherein said conduit means includes a filter to reduce the osmotic concentration of said solution being transferred to said envelope portion.

4. A surgically implantable device for expanding soft tissues as set forth in claim 1 wherein said envelope portion is made of a first material and said window portion is made of a second material.

5. A surgically implantable device for expanding soft tissues as set forth in claim 1 wherein said window portion is made of polysulfone.

6. A surgically implantable device for expanding soft tissues as set forth in claim 1 wherein said osmotic material is albumin.

7. A surgically implantable device for expanding soft tissues as set forth in claim wherein said envelope portion and said window portion are constructed of a singular material, a portion of said material being physically modified to alter its permeability characteristics and thereby form said window portion.

8. A surgically implantable device for expanding soft tissues as set forth in claim 7 wherein said physical modification is a reduction in the thickness of said material.

9. A surgically implantable device for expanding soft tissues as set forth in claim 7 wherein said physical modification is the suspension of salt in said material during the fabrication of said device.

10. A surgically implantable device for expanding soft tissues as set forth in claim 1 wherein said device further comprises a base and means for attaching said envelope to said base said base limiting the direction of said envelope expansion.

11. A surgically implantable self-inflating tissue expansion device comprising:
   a window portion being highly permeable to extracellular body fluids;
   an expandable envelope portion being substantially impermeable to extracellular body fluids, said envelope having a region defining an opening and said window extending over said opening and being attached to said envelope to thereby form an expandable balloon; and an osmotic agent contained within said balloon enabling the development of osmotic pressure across said window to draw extracellular body fluid into said balloon thus causing said balloon and overlying tissue to expand.

12. A surgically implantable tissue expansion device as set forth in claim 11 wherein said window portion is polysulfone.

13. A surgically implantable tissue expansion device as set forth in claim 11 wherein said envelope portion is silicone rubber.

14. A surgically implantable tissue expansion device as set forth in claim 11 wherein said window portion and said envelope portion are of the same material, said window portion being physically treated to enhance the permeability characteristics of said material in said window portion.

15. A surgically implantable tissue expansion device as set forth in claim 14 wherein said physical treatment of said window portion is accomplished by a method selected from the following: decreasing the thickness of said material, suspending an osmotic agent in said material during fabrication.

16. A surgically implantable tissue expansion device as set forth in claim 11 wherein said device further comprises a base attached to said balloon for limiting the direction of said expansion.

17. A self-inflating soft tissue expansion device for surgical implantation, said device comprising:

a expandable envelope portion being of a material substantially impermeable to extracellular body fluids and having a region defining an opening;

a window portion extending over said opening and being of a material permeable to extracellular body fluids;

a substantially rigid frame adhesively attached to said envelope and circumscribing said window, said frame having means for securing said window to said envelope to thereby form an expandable balloon; and an osmotic agent contained within said balloon, said osmotic agent developing an osmotic potential across said window thereby drawing said extracellular body fluids into said balloon through said window and subsequently causing said device to inflate and expand said tissue overlying said device.

18. A self-inflating soft tissue expansion device as set forth in claim 17 wherein said means for securing said window includes a tongue and groove engagement between said window and said frame.

19. A self-inflating soft tissue expansion device as set forth in claim 17 wherein said device further comprises a substantially rigid base and means for attaching said base to said envelope thereby limiting the direction in which said envelope may expand.

20. A self-inflating soft tissue expansion device as set forth in claim 19 wherein said means for attachment includes projections on said envelope and receiving cavities in said base, said projections being fixably retained within said cavities.

* * * * *